United States Patent [19]

Pichot et al.

[11] Patent Number: 5,051,748
[45] Date of Patent: Sep. 24, 1991

[54] DEVICE FOR TRANSMITTING AND RECEIVING MICROWAVE RADIATION, FOR FORMING IMAGES OF BURIED OBJECTS

[75] Inventors: Christian Pichot, Saint-Germain-en-Laye; Luc Chommeloux, Versailles; Dominique Picard, Bagneux; Jean-Charles Bolomey, Paris, all of France

[73] Assignees: Centre National de la Recherche Scientifique; Etat-Francais-Laboratoire Central Ponts et Chaussees, both of Paris, France

[21] Appl. No.: 388,945

[22] Filed: Aug. 3, 1989

[30] Foreign Application Priority Data

Aug. 3, 1988 [FR] France ................. 88 10479

[51] Int. Cl.$^5$ .................... G01S 13/04; G01V 3/12
[52] U.S. Cl. ..................................... 342/22; 324/462
[58] Field of Search ................ 342/22; 343/786, 719, 343/785, 776, 754, 909; 324/637, 639, 641, 642, 644

[56] References Cited

U.S. PATENT DOCUMENTS

| | | | |
|---|---|---|---|
| 2,075,808 | 4/1937 | Fliess | 342/22 |
| 2,897,491 | 7/1959 | Young, Jr. | 343/776 |
| 3,392,384 | 7/1968 | Wesch | 342/22 |
| 3,545,001 | 12/1970 | Giller | 343/776 |
| 3,569,974 | 3/1971 | McLeod, Jr. | 343/754 |
| 3,611,396 | 10/1971 | Jones, Jr. | 343/786 |
| 3,665,466 | 5/1972 | Hibbard | 342/59 |
| 3,708,796 | 1/1973 | Gilbert | 343/754 |
| 3,775,765 | 11/1973 | Di Piazza et al. | 342/22 |
| 3,831,173 | 8/1974 | Lerner | 342/22 |
| 3,906,492 | 9/1975 | Narbaits-Jaureguy et al. | 343/719 X |
| 4,126,860 | 11/1978 | Sullivan et al. | 342/22 X |
| 4,161,731 | 7/1979 | Barr | 342/22 |
| 4,297,699 | 10/1981 | Fowler et al. | 342/22 |
| 4,364,008 | 12/1982 | Jacques | 342/22 X |
| 4,507,602 | 3/1985 | Aguirre | 342/22 X |
| 4,607,212 | 8/1986 | Jakkula | 342/22 X |
| 4,698,634 | 10/1987 | Alongi et al. | 342/22 |
| 4,706,031 | 11/1987 | Michiguchi et al. | 324/337 |
| 4,814,768 | 3/1989 | Chang | 342/22 |

FOREIGN PATENT DOCUMENTS

| | | |
|---|---|---|
| 0069628 | 1/1983 | European Pat. Off. |
| 2241884 | 3/1975 | France. |
| 2534698 | 4/1984 | France. |
| 8803656 | 5/1988 | World Int. Prop. O. |

OTHER PUBLICATIONS

"Radant: New Method of Electronic Scanning", by C. Chekroun, et al; Microwave Journal, 1981.

Primary Examiner—John B. Sotomayor
Attorney, Agent, or Firm—Barnes & Thornburg

[57] ABSTRACT

A transmitting antenna radiates a micro-wave field through an opening in the form of a rectangular wave-guide applied against the separation surface between a first medium, in which it is located, and a second medium, in which an object is buried. The micro-wave radiation reflected by the object is collected through the opening of a receiving antenna, also in the form of a rectangular wave-guide, applied against the radiating opening of the transmitting antenna. The collected radiation is measured at a series of points by means of pin-point antennae located in the collecting opening. Thanks to the antennae arrangement, the collected radiation can be used as such, without having to subtract therefrom the result of a reference measurement. The invention can be used particularly to obtain, non destructively, images of metal bars buried in reinforced concrete.

9 Claims, 4 Drawing Sheets

DEVICE FOR TRANSMITTING AND RECEIVING MICROWAVE RADIATION, FOR FORMING IMAGES OF BURIED OBJECTS

BACKGROUND OF THE INVENTION

1. Field of the Invention

The invention relates to a device for transmitting and receiving radiation, disposed in a first medium for forming, from this first medium, an image of an object buried in a second medium.

2. Description of the Prior Art

The invention applies particularly to the case where it is desired to obtain non destructively an image of the bars and networks of metal bars embedded in concrete, for surveying, maintaining, repairing or reinforcing reinforced concrete works or buildings, for which for example no plan exists. In this case it is important to have an apparatus for determining the diameter, number and position of the bars in the concrete without having to make windows for laying bare the reinforcements locally, which is fastidious and sometimes dangerous. Naturally, the invention may apply to any other field in which it is useful to be able to form non destructively images of buried objects.

Devices of the above defined type are known which use a low frequency magnetic field and the disturbance thereof by any metal object disposed in its vicinity. These devices are known by a man skilled in the art under the name of "pachymeters" or "profometers". They are able to give indications about the position of the reinforcement the closest to the walls, and it is generally possible to determine, using charts, the diameter of a bar if the thickness of the concrete which surrounds it is known and conversely. However, in practice, the accuracy of these devices is such that they make it possible to detect the presence or absence of metal bars, in a certain volume, without it being really possible to know the number, depth and diameter thereof. Devices are also known based on the use of gamma rays or X rays, as in radiography or radioscopy systems in the medical field. However, these devices which use powerful sources for producing the radiation are very heavy and very expensive to use and require numerous and qualified staff. In addition, they are not without risks of irradiation. Moreover, on the negatives obtained, it is often impossible to interpret the image in the zones with high reinforcement density, and delicate to determine accurately the diameter of the bars whose position with respect to the source is unknown. Finally, these devices operate by transmission, which complicates the positioning and raises certain problems if the volume to be sounded is thick.

The present invention overcomes the above drawbacks by providing a device of the above defined type making possible accurate and rapid determination of the location and shape of the objects to be examined, working by reflection for easy positioning while being practically without danger for the operating staff, portable and of moderate cost.

SUMMARY OF THE INVENTION

For this, the present invention provides a device of the above defined type, characterized by the fact that it comprises:

a micro-wave source, at least one transmitting antenna connected to the source and having a radiating opening substantially in the form of a rectangular wave-guide, applied against the surface which separates the first medium from the second medium, at least one receiving antenna having a collecting opening substantially in the form of a rectangular wave-guide applied against the separation surface and disposed so that a large side of said radiating opening and a large side of said collecting opening are side by side, said receiving antenna comprising a line of pinpoint antennae disposed in said collecting opening and an output delivering a collected micro-wave signal, means for successively modulating the impedance of each of said pinpoint antennae by means of a low frequency signal, and means for determining, in response to said collected micro-wave signal and said low frequency signal, the micro-wave field at the position of each of said pinpoint antennae.

In the device of the invention, the radiation used is micro-wave radiation, transmitted by the transmitting antenna. This transmitted radiation, when it reaches the separation surface, is partially transmitted into the second medium, for example concrete. This transmitted radiation is partially reflected towards the separation surface whenever it meets, in the concrete, a discontinuity of permittivity or conductivity, for example. An object buried in the concrete is obviously at the origin of such discontinuities which may then be detected from the knowledge of the reflected radiation to which they give rise. The receiving antenna collects this reflected radiation and makes it possible, with the pinpoint antennae, to measure at a plurality of points the corresponding field related to the presence of the buried object, for forming an image of this object. The spatial resolution, particularly in the direction perpendicular to the separation surface, of such an image representative of the permittivity and of the conductivity of the material, may in particular be improved, from the results of a series of measurements at different micro-wave frequencies, using the method set forth in the article: "Electromagnetic Modelling for Microwave Imaging of Cylindrical Buried Inhomogeneities" by L. CHOMMELOUX, C. PICHOT and J. C. BOLOMEY in IEEE Transactions on Microwave Theory and Techniques, vol MTT-34, no. 10, Oct. 1986.

In the device of the invention, the micro-wave radiation used is practically without danger and the micro-wave components used are of a weight compatible with the mobility of the device and of a moderate cost. Because the wavelength of the micro-wave radiation in the material considered is relatively small, the resolution obtained is satisfactory. In addition, the type and arrangement of the transmitting and receiving antennae make measurements possible by reflection, so requiring no fastidious positioning but nevertheless being accurate, simple and rapid, because the radiation collected by the receiving antenna represents mainly the useful radiation, i.e. that which comes from reflections from the buried object.

In fact, a problem which arises when it is desired to make measurements by reflection as above, is the presence of parasite micro-wave radiation, which comes from the reflection of the radiation transmitted by the transmitting antenna from the separation surface. This radiation is useless for the measurement since, not penetrating into the second medium, it carries no useful information. However, it is directed in the same direction as the useful information and generally, by trying to measure the latter, what is in fact measured is the sum of the useful radiation and the parasite radiation. It is also said that the superimposition of the response from the separation surface or interface and the response from the object is measured. In such a case, in order to separate the response of the object from the response of the interface, it is possible to make a reference measurement, the device being disposed in a zone of the separation surface chosen so that the second medium comprises no buried object in the vicinity of this zone so as to determine the response of the interface. Then, from the result of the overall measurement is subtracted the result of the reference measurement, so as to know the response of the object. Such a method is obviously timewasting and complicated to use, and inaccurate particularly because of the variations of the response of the interface between the reference measurement and the overall measurement.

In the device of the invention, the problem does not arise for it is not necessary to make a reference measurement. In fact, because the transmitting antenna ends in a radiating opening applied against the interface, the major part of the radiation reflected by the interface remains confined inside the transmitting antenna and only a residual part of this parasite radiation, which is little troublesome, is collected by the receiving antenna which, on the other hand, because of its shape and arrangement, efficiently collects the radiation relative to the buried object. Thus, in the device of the invention, it is not necessary to make a reference measurement, which provides an appreciable gain in the time required for the measurement its simplicity and accuracy.

Advantageously, a layer of material absorbing the micro-wave radiation is inserted between the large side of said radiating opening and the large side of said collecting opening which are side by side. In this case, the transmitting antenna and the receiving antenna are very well decoupled from each other and do not influence each other. In particular, the residual part of the response of the interface which is collected by the receiving antenna is further reduced and the accuracy of the measurements is thus improved.

Advantageously again, said pinpoint antennae are buried in a dielectric strip adapted for matching said receiving antenna to said second medium.

In this case, the part of the useful radiation which is reflected from the separation surface while passing from the second medium, for example concrete, to the first medium, for example the ambient air, is reduced and the portion transmitted towards the receiving antenna increased, which increases the level of the field, so the sensitivity. In addition, the matching strip holds said pinpoint antennae in position and protects them mechanically, which antennae are for example of the electric doublet type, each being loaded at its center by a diode.

In the preferred embodiment, a single receiving antenna is provided and two transmitting antennae disposed symmetrically with respect to said receiving antenna.

In this embodiment, the symmetry of illumination gives a better determination of the volume section analyzed and so more accurate location of a buried object or objects.

In another embodiment, a plurality of transmitting antennae and a plurality of receiving antennae are provided which are alternated.

In this case, the volume section analyzed is very thick, and an image of this thick section may be obtained without moving the device.

Advantageously still:

the means for determining the field comprise means for the micro-wave synchronous detection of said collected micro-wave signal followed by low frequency processing and detection means, said micro-wave source, said transmitting antenna, said receiving antenna and said micro-wave synchronous detection means are all secured to a first portable chassis for being moved to different positions of said separation surface, and said modulation means and said low frequency processing and detection means are connected to said first chassis by at least one flexible cable.

Thus, the movement of the antennae for making measurements at different zones of the separation surface causes no disturbance in the micro-wave circuits Advantageously again, said transmitting and receiving antennae are wide band antennae.

In this case, the method mentioned for improving the spatial resolution of the image from a series of measurements made at different micro-wave frequencies may be used by software loaded in a machine disposed downstream of the device, the assembly being easily arranged so that the series of measurements and processing thereof are carried out automatically.

BRIEF DESCRIPTION OF THE DRAWINGS

The present invention will be better understood from the following description of several embodiments of the device of the invention with reference to the accompanying drawings in which.

DESCRIPTION OF THE PREFERRED EMBODIMENTS

Figure 1:
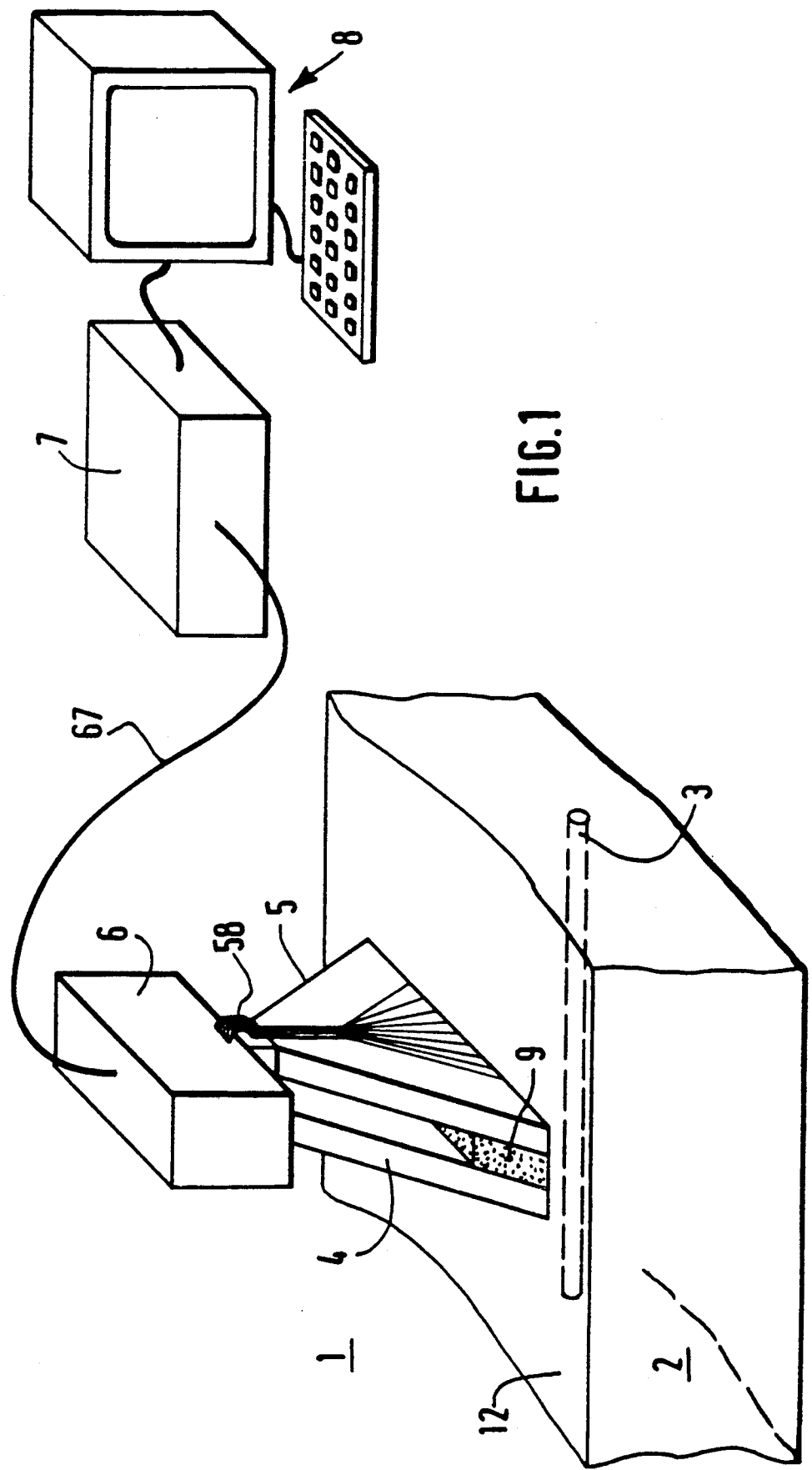
FIG. 1 is a perspective view of the device of the invention.

Referring to FIG. 1, a transmitting-receiving device is shown which, disposed in the ambient medium 1, makes it possible to form an image of one or more metal reinforcements 3 buried in a block of reinforced concrete 2, in particular for determining the precise location and diameter of the reinforcements, without for example having to destroy a part of the concrete 2.

The device comprises here a measuring head including principally a micro-wave electronic circuit 6, a transmitting antenna 4 and a receiving antenna 5. This measuring head is connected, by a flexible cable 67, to a low frequency electronic circuit 7, followed by a processing and display unit 8.

The measuring head is portable for exploring the whole of the separation surface 12, or interface, between the ambient medium 1 and concrete 2, if that is necessary, whereas the circuit 7 and unit 8 remain in the same position.

Figure 2:
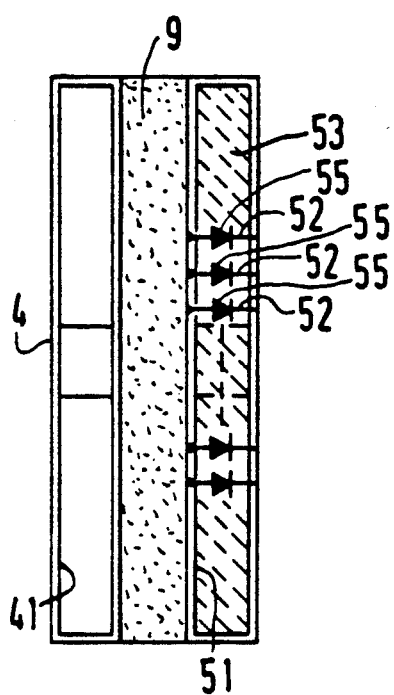
FIG. 2 is a bottom view of the measuring head of the device of FIG. 1.

The transmitting antenna is a micro-wave sectorial horn extending in plane H and which, as shown in FIG. 2, ends in a radiating opening 41 substantially in the form of a rectangular wave-guide.

In operation, opening 41 is applied against the separation surface 12. The height of horn 4 and the length of opening 41 are here substantially equal to 20 $\lambda o$, $\lambda o$ designating the wavelength of the micro-wave radiation in the ambient medium, in this case air, for the central operating frequency Of of the device. Thus, if the central frequency is chosen for example equal to 10 GHz, the wavelength $\lambda o$ is equal to 3 cm and the height of horn 4, as well as the length of opening 41, are equal to 60 cm. The width of opening 41, which corresponds to the thickness of horn 4, is here about 1 cm.

The receiving antenna 5 is a horn identical to horn 4 and so has a collecting opening 51 substantially in the form of a rectangular wave-guide as shown in FIG. 2. As is clear from this figure, and even more so from FIG. 3, a dielectric strip 53 is disposed in the collecting opening 51 of antenna 5. The thickness and the dielectric properties of strip 53 are determined so that the receiving antenna is matched to the concrete 2 when, in normal operation, opening 51 is applied against the separation surface 12 Such matching means that the radiation from the concrete 2, directed towards the inside of horn 5, undergoes as small a reflection as possible during the change of medium, and so can be collected by the horn 5 with a good level.

It is possible for a man skilled in the art to determine the thickness and the dielectric properties of strip 53 as a function of the properties of air and concrete, using for example the method described in the work: "Micro-wave Filters, Impedance Matching Networks and Coupling Structures" by G. L. MATHAEI et al, MAC GRAW HILL, (1964).

Here, a plurality of pinpoint antennae 52, disposed in a straight line, is buried in the strip 53 disposed in the collecting opening 51. Each of the pinpoint antennae 52 is of the electric doublet type loaded at its center by a PIN diode. The strands of each doublet antenna 52 are parallel to the direction of the electric field in horn 5, i.e. perpendicular to the plane of the horn. Each antenna 52 has a strand connected to ground, for example by soldering the end of this strand to the edge of the opening 51 and its other strand is connected to a conductor of a harness 58, forming part of the flexible cable 67.

The pinpoint antennae 52 are here disposed in the central part of opening 51 so as to occupy in all a length equal to half that of the opening, here 10 $\lambda o$, namely 30 cm. The antennae 52 are here 64 in number and so their alignment spacing is close to $\lambda o/6$ namely here 0.5 cm.

Figure 3:
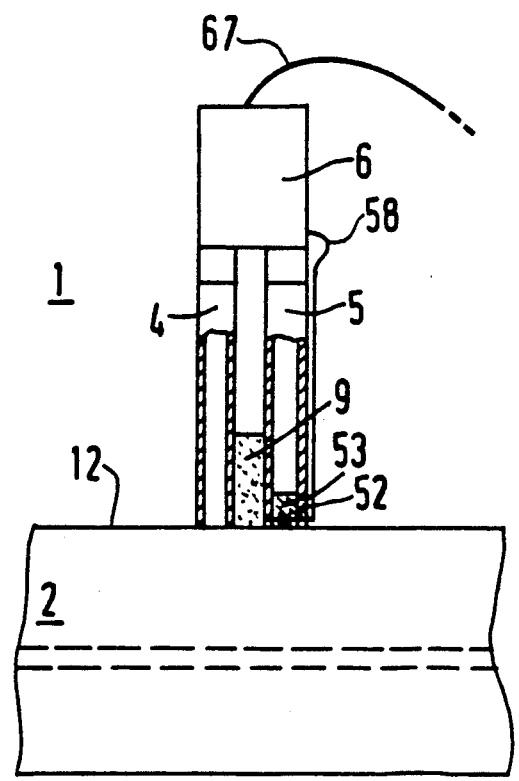
FIG. 3 is a side view, in partial section, of the measuring head of FIG. 2.

As shown in FIGS. 1, 2 and 3, the collecting opening 51 is disposed so that one of its large sides and one of the large sides of the radiating opening 41 are side by side. Here, a layer 9 of a material absorbing the microwave radiation, in the range of working frequencies, for example a carbon charged plastic material foam, is inserted between these two large sides of the openings 41 and 51. The thickness of this layer 9 is here of the same order of size as the thickness of horns 4 and 5 and the height of this layer, or more exactly its dimension perpendicular to the surface 12 is about $\lambda o$, namely 3 cm.

The transmitting antenna 4 and the receiving antenna 5 are joined to the micro-wave circuit 6, by mounting them on a common chassis. The transmitting antenna 4 receives a transmitted micro-wave signal ME from circuit 6 and the receiving antenna 5 delivers to this circuit 6 a collected micro-wave signal MC.

Figure 4:
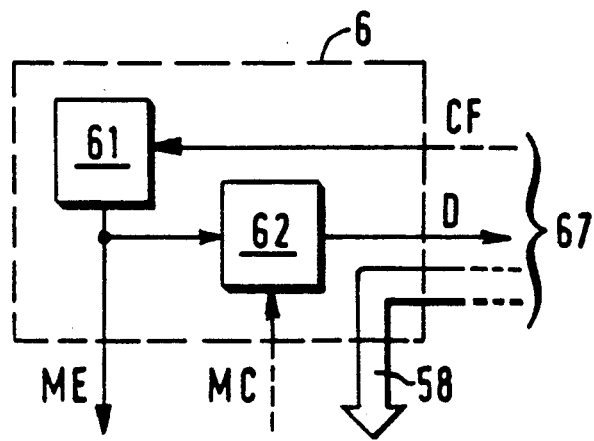
FIG. 4 is a block diagram of the micro-wave circuit of the measuring head of the device of FIG. 1.

As shown in FIG. 4, the micro-wave circuit 6 comprises a micro-wave source 61 and a micro-wave synchronous detection circuit 62. The micro-wave source 61 delivers the signal ME of frequency F between 0.7 Fo and 1.3 Fo, here 7 and 13 GHz respectively. The frequency of signal ME is controlled by a signal CF, for example a digital signal, supported by one or more conductors forming part of cable 67. The wide band circuit 62 receives the signal ME and the signal MC and delivers a signal D to one of the conductors of cable 67.

Figure 5:
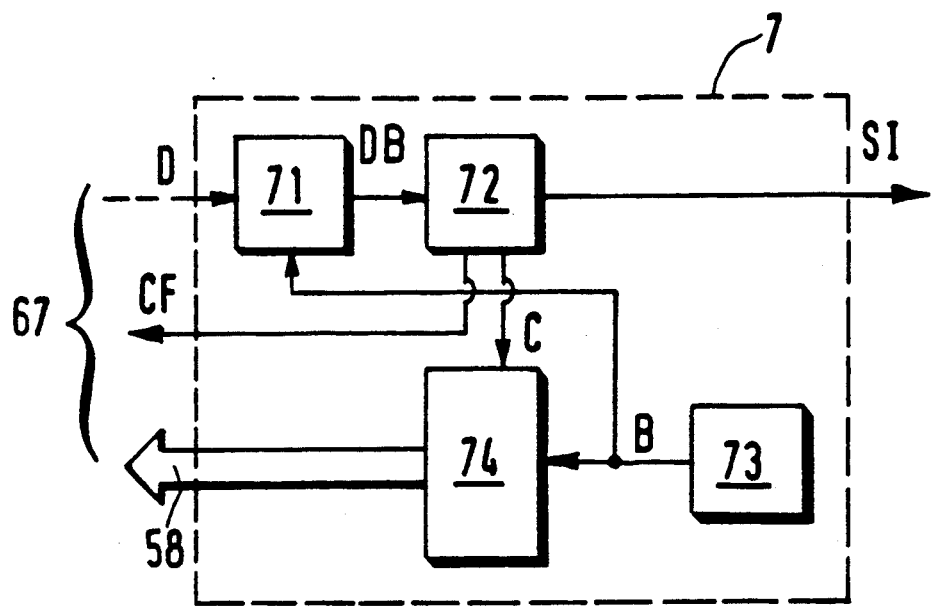
FIG. 5 is a block diagram of the low frequency circuit of the device of FIG. 1.

As shown in FIG. 5, the low frequency circuit comprises a low frequency synchronous detection circuit 71, a processing and control circuit 72, a low frequency generator 73, and a multiplexer 74.

The low frequency generator 73 delivers a low frequency signal B. By "low frequency signal" is meant here a periodic square or sinusoidal signal whose frequency range is considerably lower than the frequency range usually called micro-wave. Thus, since we may assume that the micro-wave range is limited towards the bottom to several hundred megahertz, signal B will in general have a frequency less than a few tens of megahertz.

The low frequency synchronous detection circuit 71 has an input receiving the signal D, an input receiving the signal B and an output delivering the signal DB.

The multiplexer 74 has a single input receiving signal B, a plurality of outputs connected to the conductors of harness 58, and a control input receiving a digital signal C.

The processing circuit 72, controlled by a microprocessor for example, has an input receiving the signal DB and three outputs delivering the digital signals CF, C and a signal SI also digital representative of the micro-wave field measured.

The display and processing unit 8 receives the signal SI and executes a software for implementing the process, already mentioned, for improving the spatial resolution of the image and displays this image on the screen with which it is provided.

The device which has just been described operates as follows.

The processing circuit 72 first of all controls, through the signal CF, the micro-wave source so that its value is for example 7 GHz.

The resultant micro-wave radiation is transmitted by horn 4 and is partially reflected by the separation surface 12 and partially transmitted into the concrete 2.

The reflected part remains confined inside the transmitting horn 4 or is absorbed by layer 9, which means that a very small part only of this parasite radiation reaches the receiving horn 5.

On the other hand, the part of the transmitted radiation which is transmitted into the concrete is reflected from object 3 and gives rise to a reflected radiation collected by horn 5.

Simultaneously, the processing circuit 72 controls the multiplexer so that the signal B is applied to one only of diodes 55. Thus, only this diode is biassed, successively forwardly and reversely, at the rate of signal B.

In circuit 62, the collected micro-wave signal MC undergoes micro-wave synchronous detection by means of the micro-wave signal ME then the resultant signal D undergoes, in circuit 71, low frequency synchronous detection by means of signal B. Now, only the part of the collected radiation from the doublet antenna 52 loaded by diode 55, which is biassed by signal B, is modulated by this signal B. Thus, the signal MC, after micro-wave then low frequency detection, is only representative of the field at the point where is situated the doublet antenna 52 loaded by diode 55 which is biassed by signal B. The microprocessor of circuit 72 may then control the successive biassing of each of diodes 55 and form the signal SI from the signal C which indicates the position of the measuring point and from the signal resulting from the double detection which indicates the value of the field at this measuring point.

This type of operation results from the use of the method known by a man skilled in the art under the name of "modulated diffusion method".

After this first measurement at 7 GHz, circuit 72 controls a variation of the frequency of source 61 so as to obtain the same results for another value of the frequency, and so on, in order for example to permit unit 8 to use the resolution improvement method already mentioned. Thus, in each of the two directions of a plane parallel to the plane of horns 4 and 5 a resolution is obtained of the order of the minimum half wavelength in the concrete, which corresponds, for the frequency range 7–13 GHz and assuming for the concrete a relative dielectric constant of 6, to a value of about 0.5 cm., which corresponds obviously to the alignment pitch of the doublet antennae 52.

Figure 6:
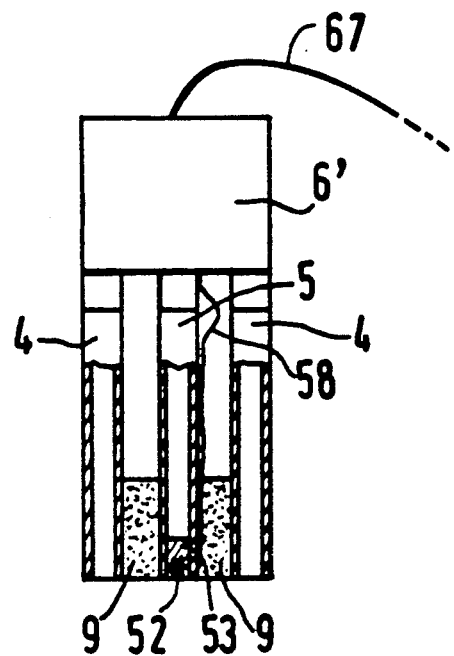
FIG. 6 is a side view, in partial section, of a first variant of the measuring head of FIG. 2.

In FIG. 6 a particularly advantageous variant of the measuring head has been shown, for which two transmitting antenna 4 are provided, identical to the one which has just been described, disposed symmetrically with respect to a single receiving antenna 5, which is itself identical to that which has just been described. This symmetrical arrangement makes it possible to eliminate certain parasite signals and to improve the definition in the direction perpendicular to the plane of horns 4 and 5. The corresponding micro-wave circuit 6' is adapted accordingly.

Figure 7:
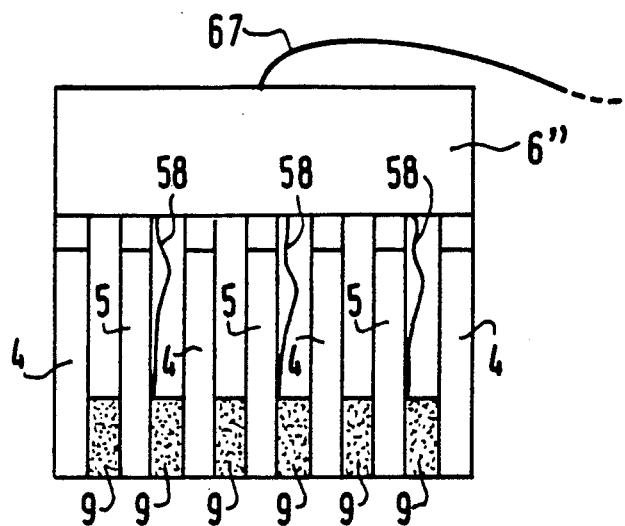
FIG. 7 shows a side view of a second variant of the measuring head of FIG. 2.

Similarly, in FIG. 7, another variant of the measuring head has been shown in which a plurality of transmitting antennae 4 have been provided, all identical to the one which has just been described and a plurality of receiving antennae, all identical to the one which has just been described, juxtaposed in an alternating way. The corresponding micro-wave circuit 6'' is adapted accordingly.

Figure 8:
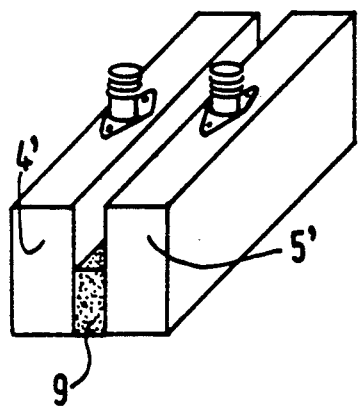
FIG. 8 shows a perspective view of a variant of the antennae of the device of FIG. 1.
Figure 9:
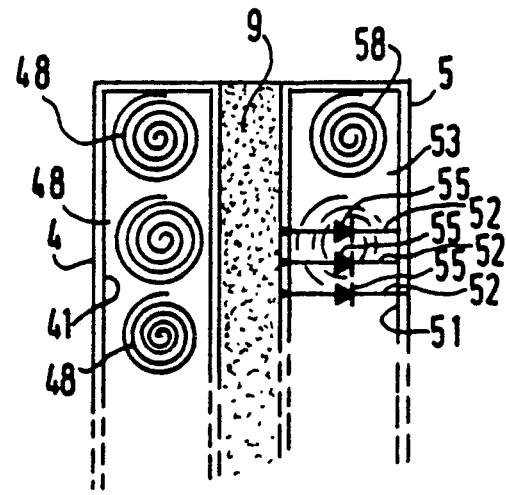
FIG. 9 is a bottom view of the antennae of FIG. 8.

In FIGS. 8 and 9 variants 4' and 5' have been shown of the transmitting and receiving antennae 4 and 5. It is still a question, as for horns 4 and 5, of wide band antennae, but they are each formed from a wave-guide section open at one end and having, at the other end, a network of wide band elementary antennae, such as spiral antennae 48 and 58, for example.

As for horns 4 and 5, the large dimension of the section of the wave-guide length is here equal to 20 λo. Such a value is however not imperative, it is sufficient for this large dimension to be from one to a few tens of λo. The small dimension of the section of the guide lengths is here laid down by the size of antennae 48 and 58.

Naturally, the scope of the present application is not limited to the description which has just been made.

Thus, for the sake of simplification, the signals for low frequency biassing of the diodes have been described using a single wire harness. In practice, and as a man skilled in the art may readily understand, it is advantageous to feed these these biassing signals through low-pass filters, which behave as short-circuits for the low frequency signals, and as open circuits for the microwave signals. These filters may advantageously be in the form of micro-wave strips or striplines, for example, disposed along the walls of horns 4 and 5 or sections of antennae 4' and 5'.

Similarly, it is not obligatory to use PIN diodes, and they may be replaced by photodiodes which are biassed by a laser beam or optical fibers.

Similarly, it is not obligatory to systematically use the improvement and resolution algorithm, it is also possible to work at a single frequency by directly displaying the signal SI.

Finally, the applications of the device of the invention are obviously not limited to the non destructive sounding of reinforced concrete. In particular, it is within the scope of a man skilled in the art to transpose the wavelengths used as a function of the size, nature and depth of the structures to be detected, but also of the electromagnetic properties of the medium in which they are buried.

What is claimed is:

1. A device, disposed in a first medium, for transmitting and receiving radiation and for forming an image of an object buried in a second medium, comprising:
    a micro-wave source,
    at least one transmitting antenna connected to the source and having a radiating opening substantially in the form of a rectangular wave-guide, applied against a surface which separates the first medium from the second medium,
    at least one receiving antenna having a collecting opening substantially in the form of a rectangular wave-guide applied against the separation surface and disposed so that a large side of said radiating opening and a large side of said collecting opening are side by side, said receiving antenna comprising a line of pinpoint antennae disposed in said collecting opening and an output delivering a collected micro-wave signal,
    means for modulating the impedance of each of said pinpoint antennae successively by a low frequency signal, and
    means for forming said image of an object buried in the second medium in response to said collected micro-wave signal at the position of each of said pinpoint antenna and said low frequency signal.

2. The device as claimed in claim 1, wherein a layer of material absorbing the micro-wave radiation is inserted between the large side of said radiating opening and the large side of said collecting opening which are side by side.

3. The device as claimed in claim 1, wherein said pinpoint antennae are buried in a dielectric strip adapted for matching said receiving antenna to said second medium.

4. The device as claimed in claim 1, comprising a single receiving antenna and two transmitting antennae, disposed symmetrically with respect to said receiving antenna.

5. The device as claimed in claim 1, comprising a plurality of transmitting antennae and a plurality of receiving antennae, which are alternated.

6. The device as claimed in claim 1, wherein:
    said means for forming the field comprise means for the micro-wave synchronous detection of said collected micro-wave signal followed by low frequency processing and detection means, said micro-wave source, said transmitting antenna, said receiving antenna and said micro-wave synchronous detection means are all secured to a first chassis which is portable for being moved to different positions of said separation surface, and said modulation means and said low frequency processing and detection means are connected to said first chassis by at least one flexible cable.

7. The device as claimed in claim 1, wherein said transmitting and receiving antennae are wide band antennae.

8. The device as claimed in claim 7, wherein said transmitting and receiving antennae are horns and the large dimension of said radiating opening and of said collecting opening is from one to a few tens of wavelengths of the micro-wave radiation in said first medium.

9. The device as claimed in claim 7, wherein said transmitting and receiving antennae are wave-guide sections, open at one end, and having at the other end a network of wide band antennae and the large section dimension of said wave-guide is from one to a few tens of wavelengths of the micro-wave radiation in said first medium.

* * * * *